United States Patent [19]

Shinohara et al.

[11] Patent Number: 4,985,577

[45] Date of Patent: Jan. 15, 1991

[54] 3-(3,4-DIMETHOXYPHENYL)PROPYLTRI-CHLOROSILANE

[75] Inventors: Toshio Shinohara, Takasaki; Yoshifumi Inoue, Annaka, both of Japan

[73] Assignee: Shin-Etsu Chemical Co., Ltd., Tokyo, Japan

[21] Appl. No.: 371,780

[22] Filed: Jun. 27, 1989

[30] Foreign Application Priority Data

Jun. 28, 1988 [JP] Japan .................. 63-158118

[51] Int. Cl.$^5$ .............................................. C07F 7/08
[52] U.S. Cl. ................................................... 556/445
[58] Field of Search .................. 556/445, 410, 412

[56] References Cited

PUBLICATIONS

Noll, "Chemistry and Technology of Silicones", Academic Press, N.Y., (1968), pp. 103 and 148.

Primary Examiner—Paul F. Shaver
Attorney, Agent, or Firm—Millen, White & Zelano

[57] ABSTRACT 3-(3,4-Dimethoxyphenyl)propyltrichlorosilane, which in a new material, was disclosed together with some ways to synthesize it. A usefulness thereof was illustrated by synthesizing polysilazane using the above new material and applying the polysilazane to a steel plate as a protective coat.

1 Claim, No Drawings

3-(3,4-DIMETHOXYPHENYL)PROPYLTRICHLOROSILANE

FIELD OF THE INVENTION

This invention relates to a novel organosilicon compound and, more particularly, to an organosilicon compound useful as a starting material for silicone resins, a surface treating agent, a silylating agent and carbon functionalsilane.

BACKGROUND OF THE INVENTION

The organosilicon compound provided by this invention has so far been an unknown material.

SUMMARY OF THE INVENTION

An object of this invention is to provide a novel organosilicon compound, which can replace

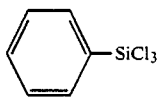

used frequently for the production of silicone resins since it has three hydrolyzable chlorines in a molecule.

In addition, silicone resins having affinity for water can be produced from the organosilicon compound of this invention, because it has two methoxy groups in a molecule.

Moreover, since the moiety SiCl in the molecule reacts readily with various compounds containing an active hydrogen atom, this compound can be used as an agent for the surface treatment of silica and titania, and silylating agent in organic syntheses.

When this compound is allowed to react with alcohols, alkoxysilanes represented by the following formula can be easily obtained:

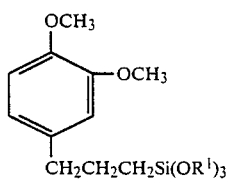

(wherein R' represents a monovalent organic group).

The thus derived alkoxysilanes are useful in particular since they can be utilized as carbon functional silanes well-known in silicone industry.

On the other hand, this compound can be utilized as a protective film for steel plate when converted to polysilazane through the reaction with ammonia.

The organosilicon compound of this invention is a novel material, and particularly useful as a raw material for syntheses of silicone resins, a surface treating agent, a silylating agent, a carbon functional silane, and the like.

DETAILED DESCRIPTION OF THE INVENTION

A novel organosilicon compound provided by this invention is 3-(3,4-dimethoxyphenyl)propyltrichlorosilane represented by the following formula,

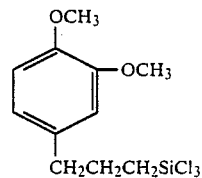

and can be synthesized by Grignard reaction or a reaction utilizing lithium described below.

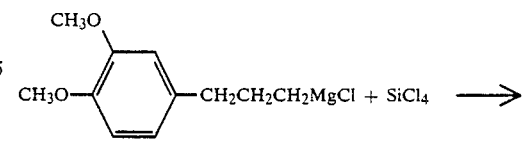

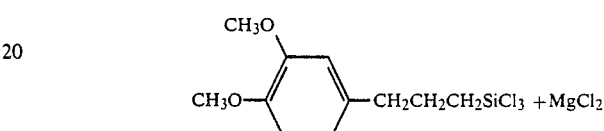

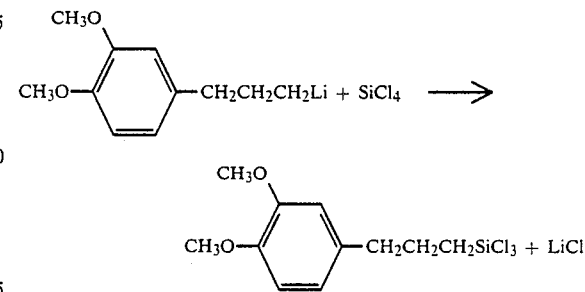

The most excellent and efficient synthesis method, as described below, consists in using chloroplatinic acid as catalyst, and causing 1-allyl-3,4-dimethoxybenzene to undergo the addition reaction with trichlorosilane:

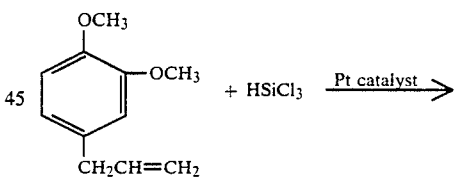

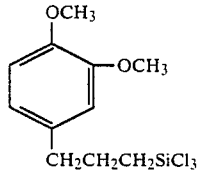

The invention will now be illustrated in more detail by reference to the following examples.

EXAMPLE 1

In a 300 ml of four-necked flask equipped with a stirrer, a reflux condenser, a thermometer and a dropping funnel, 89 g (0.5 mole) of 1-allyl-3,4-dimethoxybenzene and 0.01 g of chloroplatinic acid (H$_2$PtCl$_6$.6H$_2$O) were placed. The temperature of the flask content was raised to 80° C. with stirring.

Thereto, 68 g (0.5 mole) of trichlorosilane was added dropwise over a period of 2 hours. Thereupon, a gentle exothermic phenomenon was observed, and the temperature of the reaction system became 80°-90° C.

Thereafter, the heating was continued for 3 hours so that the reaction system might be kept at 80°-90° C.

The thus obtained reaction product was distilled under reduced pressure to yield 154 g of distilate having a boiling point of 130° C. under a pressure of 5 mmHg. The analysis by gas chromatography proved that this distilate was a single component. Product yield was 98%.

From the analysis result described below, the product was comfirmed to be 3-(3,4-dimethoxyphenyl) propyltrichlorosilane of the formula,

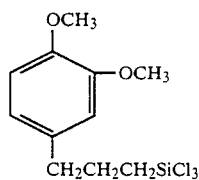

Elemental analysis:

|  | C (%) | H (%) | Cl (%) | Si (%) |
| --- | --- | --- | --- | --- |
| Anal. Calcd. | 42.1 | 4.8 | 33.9 | 9.0 |
| Found | 42.1 | 4.7 | 34.1 | 8.9 |

NMR analysis: δ(ppm) 7.1 (s, 3H, aromatic), 4.1 (s, 6H, —OCH₃), 2.9 (t, 2H,

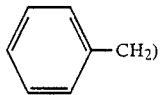

2.2 (broad, 2H, C—CH₂—C), 1.8 (broad, 2H, Si—CH₂—).

EXAMPLE 2

A 10 g portion of 3-(3,4-dimethoxyphenyl) propyltrichlorosilane prepared in Example 1 was dissolved in 100 g of toluene, and then neutralized at a temperature of 40° C. by bubbling thereinto ammonia gas in an amount larger than the prescribed one.

After NH₄Cl formed as a by-product was filtered out, toluene was further added to the thus obtained solution so as to prepare a 1% toluene solution of polysilazane on solid basis.

Ammonium sulfate as a curing catalyst was added to the toluene solution in a concentration of 0.1% to prepare a coating solution.

This coating solution was spread over a commercially available steel plate using a flow coating technique, and air-dried.

Thereafter, it was heated at 220° C. for 1 hour to form a coat.

The thus obtained coat was smooth, and excellent in heat resistance, abrasion resistance and dyeability.

From these results, the material of this invention has proved to be useful in particular as an agent for forming on a steel plate a protective coat excellent in printability.

What is claimed is:

1. 3-(3,4-Dimethoxyphenyl)propyltrichlorosilane, a compound represented by the formula,

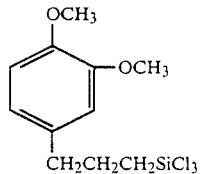

* * * * *